United States Patent
Koh et al.

(10) Patent No.: US 9,901,300 B2
(45) Date of Patent: Feb. 27, 2018

(54) MEDICAL IMAGING APPARATUS AND METHOD OF PROVIDING MEDICAL IMAGES

(71) Applicant: SAMSUNG MEDISON CO., LTD., Gangwon-Do (KR)

(72) Inventors: Dal Kwon Koh, Suwon-si (KR); Jung Taek Oh, Seoul (KR); Hyoung Jin Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 561 days.

(21) Appl. No.: 14/326,337

(22) Filed: Jul. 8, 2014

(65) Prior Publication Data
US 2015/0011872 A1 Jan. 8, 2015

(30) Foreign Application Priority Data
Jul. 8, 2013 (KR) ........................ 10-2013-0079758

(51) Int. Cl.
*A61B 5/00* (2006.01)
*A61B 5/06* (2006.01)
(Continued)

(52) U.S. Cl.
CPC .......... *A61B 5/4887* (2013.01); *A61B 5/0095* (2013.01); *A61B 5/061* (2013.01);
(Continued)

(58) Field of Classification Search
CPC ... A61B 8/4245; A61B 8/4254; A61B 8/4263; A61B 8/463; A61B 5/4887;
(Continued)

(56) References Cited

U.S. PATENT DOCUMENTS

2004/0068423 A1 4/2004 Shaw
2006/0274928 A1 12/2006 Collins et al.
(Continued)

FOREIGN PATENT DOCUMENTS

JP 2005-270328 A 10/2005
JP 2012-205886 A 10/2012
(Continued)

OTHER PUBLICATIONS

Notice of Patent Allowance KR Patent Application No. 10-2013-0079758 dated Mar. 30, 2015 with partial English translation.
(Continued)

*Primary Examiner* — Katherine Fernandez
*Assistant Examiner* — Colin T Sakamoto
(74) *Attorney, Agent, or Firm* — McDermott Will & Emery LLP

(57) ABSTRACT

Disclosed herein are an a medical imaging apparatus capable of easily detecting the location of specific tissue, for example, a lymph node, and a method of providing medical images. The medical image providing method includes: arranging and displaying n thumbnail images for n first photoacoustic images acquired by initially scanning an object, wherein n is a natural number; and enhancing a thumbnail image that is identical to a second photoacoustic image acquired by secondarily scanning the object, among the n thumbnail images.

10 Claims, 12 Drawing Sheets

(51) Int. Cl.
*A61B 8/08* (2006.01)
*A61B 6/00* (2006.01)
*A61B 8/14* (2006.01)
*A61B 8/00* (2006.01)

(52) U.S. Cl.
CPC .............. *A61B 5/418* (2013.01); *A61B 6/469* (2013.01); *A61B 8/4405* (2013.01); *A61B 8/463* (2013.01); *A61B 8/5261* (2013.01); *A61B 8/14* (2013.01); *A61B 8/56* (2013.01)

(58) Field of Classification Search
CPC ....... A61B 5/0095; A61B 5/061; A61B 5/418; A61B 6/469; A61B 8/4405; A61B 8/5261; A61B 8/56; A61B 8/14
See application file for complete search history.

(56) References Cited

U.S. PATENT DOCUMENTS

| 2009/0036902 A1* | 2/2009 | DiMaio | A61B 19/2203 606/130 |
|---|---|---|---|
| 2011/0216958 A1 | 9/2011 | Satoh et al. | |
| 2012/0176408 A1 | 7/2012 | Moriya | |
| 2014/0145648 A1* | 5/2014 | Tokita | A61B 5/0073 315/362 |
| 2015/0305718 A1* | 10/2015 | Ogasawara | A61B 8/461 600/440 |

FOREIGN PATENT DOCUMENTS

| KR | 2003-0075779 A | 9/2003 |
|---|---|---|
| KR | 10-2009-0088909 A | 8/2009 |
| KR | 10-2013-0039198 A | 4/2013 |
| WO | 2012165169 A1 | 12/2012 |

OTHER PUBLICATIONS

Communication Pursuant to Article 94(3) EPC European Patent Application No. 14 150 720.2 dated Oct. 22, 2015.

European Search Report EP Application No. 14150720.2 dated Nov. 18, 2014.

* cited by examiner

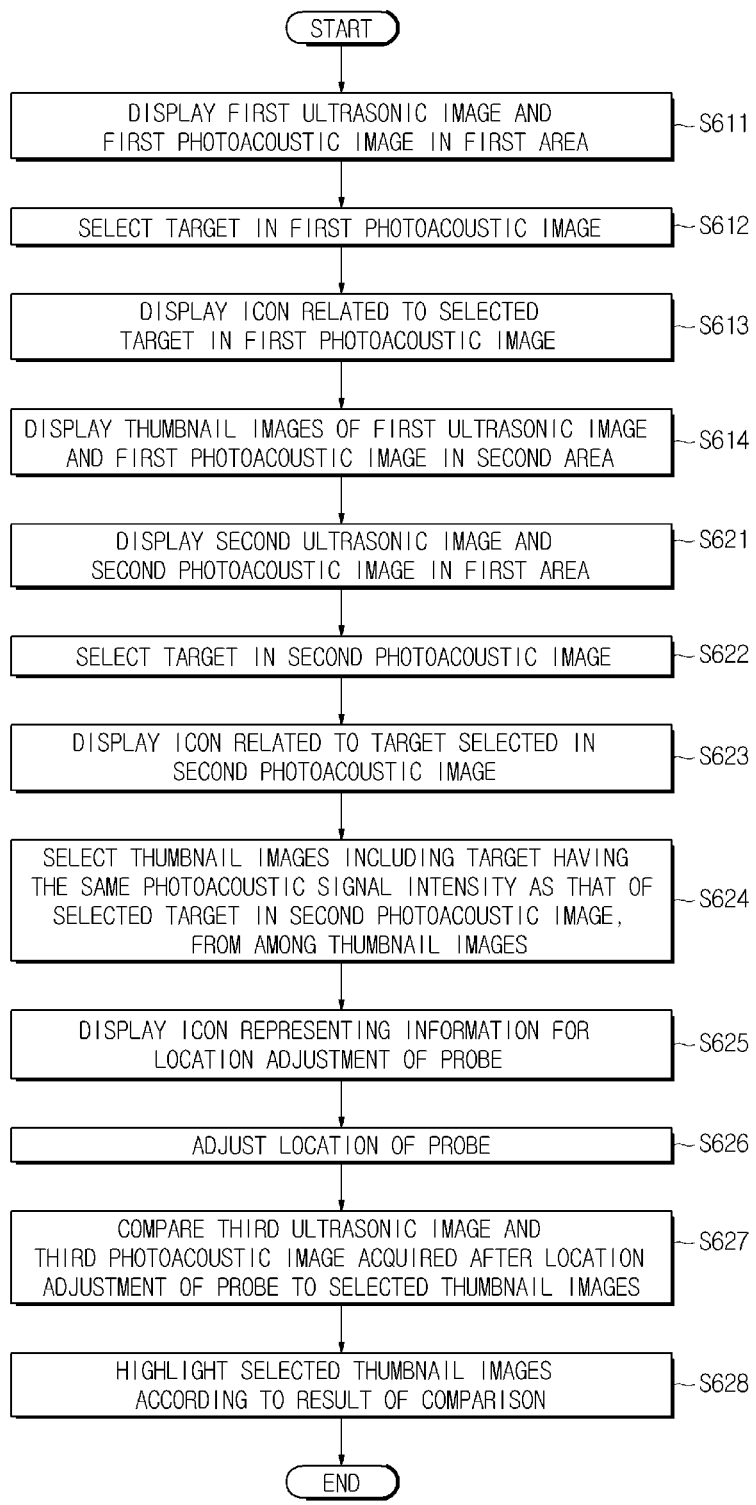

MEDICAL IMAGING APPARATUS AND METHOD OF PROVIDING MEDICAL IMAGES

CROSS-REFERENCE TO RELATED APPLICATION

This application claims the benefit of Korean Patent Application No. 10-2013-0079758 filed on Jul. 8, 2013 in the Korean Intellectual Property Office, the disclosure of which is incorporated herein by reference.

BACKGROUND

1. Field

Embodiments of the present invention relate to a medical imaging apparatus and a method of providing medical images, and more particularly, to a medical imaging apparatus capable of easily detecting the location of specific tissue, for example, a lymph node, and a method of providing medical images.

2. Description of the Related Art

Medical imaging apparatuses irradiate ultrasonic waves, laser, X-rays, or the like to a target, acquire an image of the target according to transmission, absorption, and reflection properties of the target, and use the acquired image of the target for diagnosis. The medical imaging apparatuses include an ultrasonic imaging apparatus, a photoacoustic imaging apparatus, an X-ray imaging apparatus, etc.

The photoacoustic imaging apparatus is an apparatus using a photoacoustic imaging technique. The photoacoustic imaging technique noninvasively images the inside of an object using a photoacoustic effect, wherein the photoacoustic effect is an effect in which a certain material generates acoustic waves due to momentary expansion and contraction when absorbing light or electromagnetic waves.

The photoacoustic imaging apparatus includes a light source to irradiate light to the inside of an object, and a probe to receive acoustic waves generated from the object that has absorbed the light. When a biopsy is taken using the photoacoustic imaging apparatus, first, a dye is injected to the inside of an object such that the dye is absorbed onto specific tissue, for example, a lymph node. Then, a probe is used to scan the object to acquire an image, and the acquired image is analyzed, thereby detecting the specific tissue.

SUMMARY

Therefore, it is an aspect of the present invention to provide a medical imaging apparatus capable of easily detecting the location of specific tissue, for example, a lymph node, and a method of providing medical images.

Additional aspects of the invention will be set forth in part in the description which follows and, in part, will be obvious from the description, or may be learned by practice of the invention.

In accordance with one aspect of the present invention, a medical image providing method includes: arranging and displaying n thumbnail images for n first photoacoustic images acquired by initially scanning an object, wherein n is a natural number; and enhancing a thumbnail image that is identical to a second photoacoustic image acquired by secondarily scanning the object, among the n thumbnail images.

In accordance with another aspect of the present invention, a medical imaging apparatus includes: a sensor configured to sense a location of a probe; a display unit configured to arrange and display n thumbnail images for n first photoacoustic images acquired by initially scanning an object using the probe, wherein n is a natural number; and a controller configured to enhance a thumbnail image that is identical to a second photoacoustic image acquired by secondarily scanning the object using the probe, among the n thumbnail images.

According to the medical imaging apparatus and the medical image providing method as described above, it is possible to easily detect the location of specific tissue, for example, a lymph node, and to easily determine whether breast cancer has spread based on the results of the detection.

BRIEF DESCRIPTION OF THE DRAWINGS

These and/or other aspects of the invention will become apparent and more readily appreciated from the following description of the embodiments, taken in conjunction with the accompanying drawings of which:

FIG. 6 is a flowchart of a medical image providing method according to an embodiment of the present invention.

DETAILED DESCRIPTION

Figure 1:
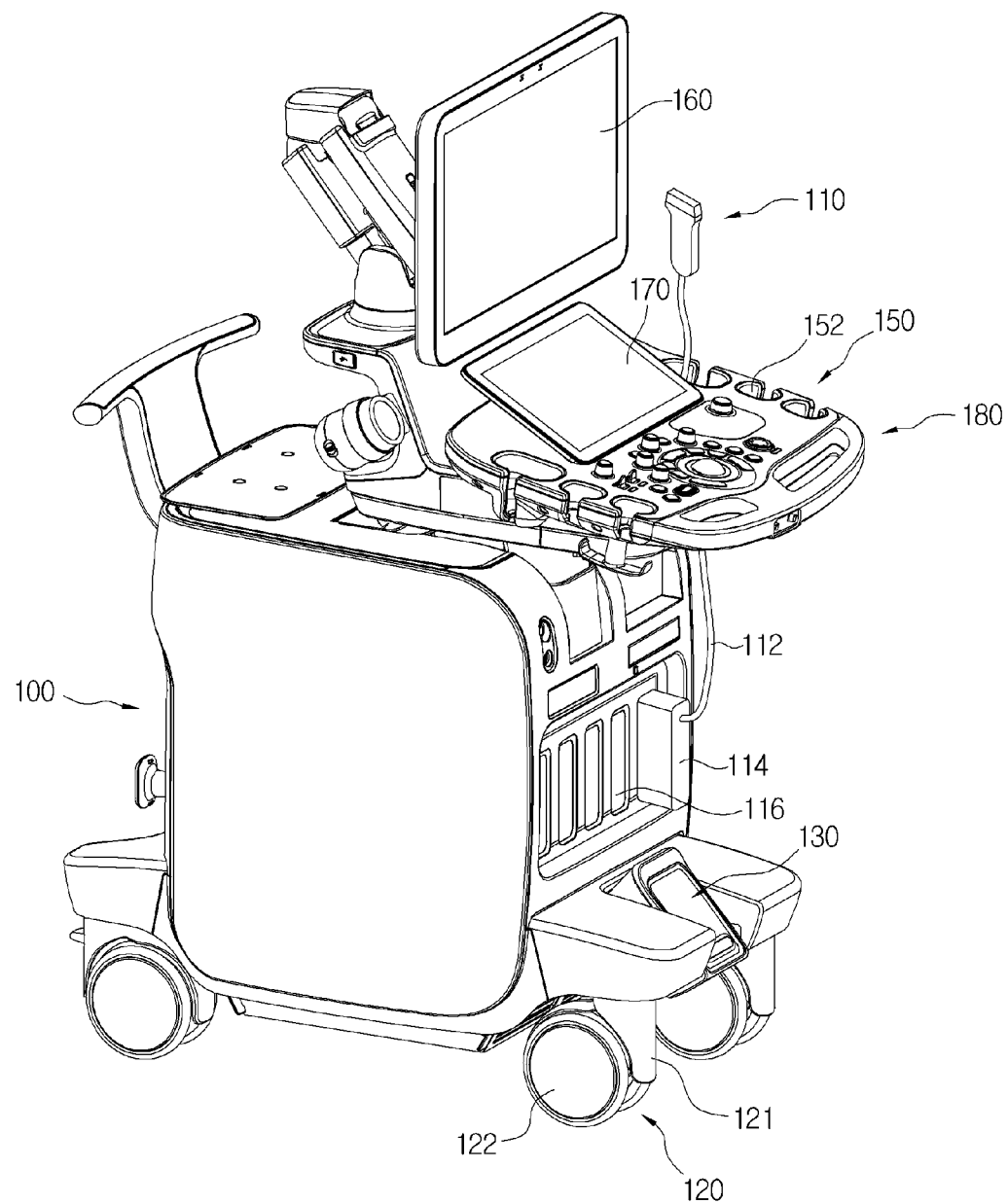
FIG. 1 is a perspective view illustrating an external appearance of a medical imaging apparatus according to an embodiment of the present invention.

Reference will now be made in detail to the embodiments of the present invention, examples of which are illustrated in the accompanying drawings, wherein like reference numerals refer to like elements throughout.

As a medical imaging technology for diagnosing an object, photoacoustic imaging (PAI) technology has been developed which diagnoses an object by combining the ultrasonic characteristics of the object with the photoacoustic characteristics of the object. The PAI technology is widely used in various medical diagnosis fields.

The PAI technology, which combines high spatial resolution of ultrasonic images with a high contrast ratio of optical images, is suitable to image biologic tissues. More specifically, when laser having a short wavelength in a unit of nanometer is irradiated to biologic tissues, the short electromagnetic pulses of the laser are absorbed in the biologic tissues, and momentary acoustic waves are generated by thermo-elastic expansion in a tissue region acting as a source of initial ultrasonic waves, wherein most of the acoustic waves is ultrasonic waves. The ultrasonic waves arrive at the biologic tissues at different times, and the ultrasonic waves are finally displayed as a photoacoustic image. In the following exemplary embodiments, the term "photoacoustic waves" mean acoustic waves generated by absorption of light, wherein the photoacoustic waves include ultrasonic waves.

Ultrasonic imaging technology is well-known and widely used technology to diagnose lesions in a human body using ultrasonic waves. Ultrasonic images are created by irradiating ultrasonic waves to an object and then receiving and imaging ultrasonic waves reflected from the inside materials of the object. The ultrasonic images include a B-mode image to represent a section of an object, an elastic image to represent elasticity information of an object, a M-mode image to represent biological information about a specific region of an object, and a color Doppler image to visualize blood flow in real time.

Photoacoustic images can be combined with ultrasonic images. For example, by irradiating ultrasonic waves to a specific region of an object to obtain an ultrasonic image, then irradiating laser to the same specific region of the object to obtain a photoacoustic image, and comparing and analyzing the two images, an absorption rate of the specific region as well as an anatomical structure of the specific region can be recognized.

FIG. 1 is a perspective view illustrating an external appearance of a medical imaging apparatus according to an embodiment of the present invention.

Referring to FIG. 1, the medical imaging apparatus includes a main body 100, a probe 110, a control panel 150, a main display unit 160, and a sub display unit 170.

The main body 100 accommodates main components of the medical imaging apparatus therein. For example, the main body 100 may accommodate a controller 190, a transmission signal generator 104, and a storage unit 105 (see FIG. 2).

The main body 100 may be in the shape of a hexahedron. In the front side of the main body 100, one or more female connectors 116 are provided. A male connector 114 connected to one end of a cable 112 is physically coupled with one of the female connectors 116. The other end of the cable 112 is connected to the probe 110.

In the lower part of the main body 100, a plurality of castor modules 120 for moving the medical imaging apparatus are provided. The caster modules 120 can fix the medical imaging apparatus at a specific location, or move the medical imaging apparatus in a specific direction. In FIG. 1, four castor modules 120 are installed in the lower part of the main body 100. However, the number of the castor modules 120 is not limited to four, and castor modules that are more or less than four castor modules may be provided according to the shape of the main body 100. Hereinafter, for convenience of description, it is assumed that four castor modules are provided in the lower part of the main body 100.

Each castor module 120 may include a castor main body 121, a castor 122, and a lever (not shown).

The castor 122 is protruded downward from the castor main body 121, and supported by the ground.

Although not illustrated in FIG. 1, one end of the lever may be connected to the castor main body 121, and the other end of the lever may be protruded upward from the castor main body 121 to turn to the rear side of the main body 100 from the front side. That is, the other end of the lever may rotate with respect to the one end of the level. If the location of the lever is a reference location when the other end of the lever has turned to the rear side of the main body 100, the lever can rotate to the left at a predetermined angle from the reference location, and also can rotate to the right at a predetermined angle from the reference location.

The location of the lever decides the state of the castor 122. The state of the castor 122 may include brake, free swivel, and directional lock (or swivel lock).

The brake is a state in which the castor 122 stops or is totally locked such that the castor 122 cannot move. The free swivel is a state in which the castor 122 can rotate while freely changing its traveling direction. The directional lock (or swivel lock) is a state in which the castor 122 may be rotated under the direction of the castor 122 fixed.

For example, when the lever is at the reference location, the castor 122 may be in the free swivel state. If the lever has horizontally turned to the left from the reference location, the castor 122 may be in the brake state. If the lever has horizontally turned to the right from the reference location, the castor 122 may be in the direction lock state. As another example, when the lever turns to the left, to the reference location, and to the right, the state of the castor 122 may change to the brake state, to the free swivel state, and to the directional lock state, respectively.

Although not illustrated in FIG. 1, the levers of two castor modules 120 positioned to the left and right in the front side of the main body 100 may be mechanically connected to each other by a link (not shown). Accordingly, a user may adjust the location of the lever of any one of the two castor modules 120 to thereby adjust the states of the two castor modules 120 at once.

In the front, lower part of the main body 100, a pedal module 130 may be provided. Although not shown in FIG. 1, the pedal module 130 may include a pedal moving up and down by external power, a power transfer unit transferring external power applied to the pedal to the levers of the castor modules 120, and a pedal cover covering the pedal and the power transfer unit. The power transfer unit may be mechanically connected to the link connecting the two castor modules 120 located in the front side of the main body 100. Accordingly, when external power is applied to the pedal, the external power applied to the pedal is transferred to the link by the power transfer unit, so that the link moves to the left and right by the external power. Due to the left and right movement of the link, the levers connected to both ends of the link move accordingly. As a result, the positions of the levers change, so that the states of the castors 122 are decided according to the positions of the levers.

Figure 2:
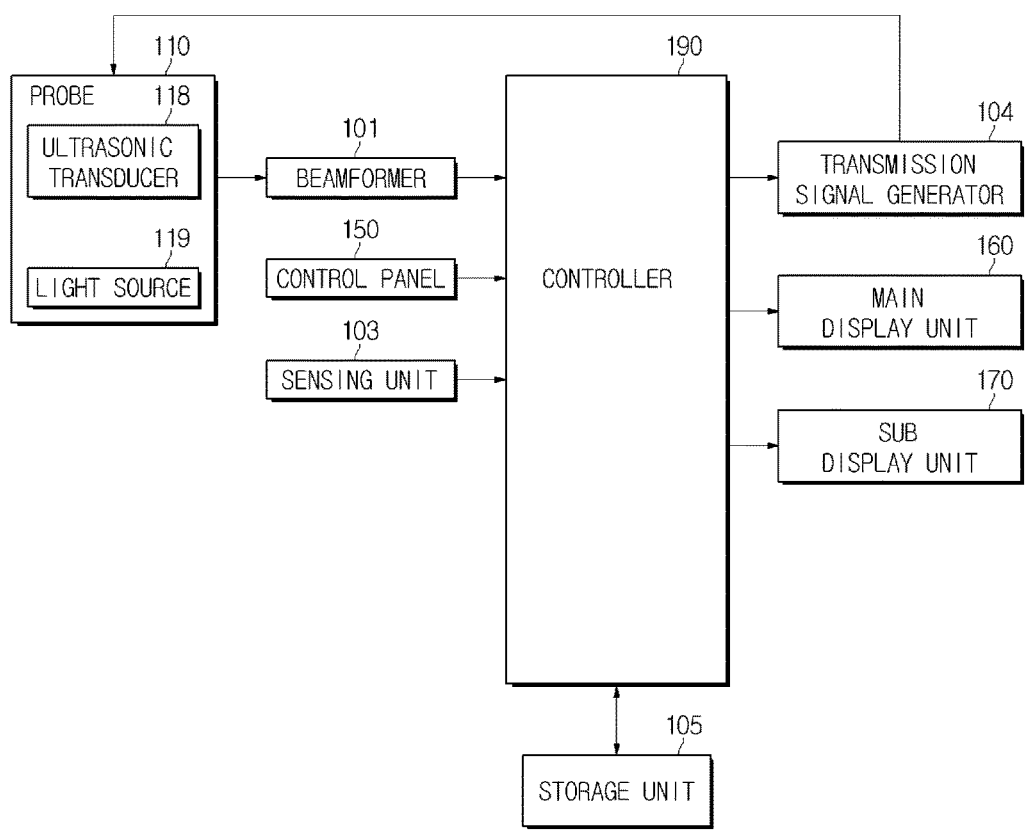
FIG. 2 is a block diagram of a control configuration of the medical imaging apparatus illustrated in FIG. 1.

The probe 110 contacts an object (for example, a patient's breast), and may include a plurality of ultrasonic transducers (118 of FIG. 2) and a light source (119 of FIG. 2).

The ultrasonic transducers 118 generate ultrasonic waves according to electrical signals received from the transmission signal generator (104 of FIG. 2), and receive ultrasonic echo signals reflected from the object.

The ultrasonic transducers 118 may generate ultrasonic waves according to alternating current power applied thereto. More specifically, the ultrasonic transducers 118 may receive alternating current power from an external power supply or from an internal power storage unit, for example, a battery. The piezoelectric vibrators or thin films of the ultrasonic transducers 118 may vibrate according to the alternating current power to generate ultrasonic waves.

Each ultrasonic transducer 118 may be a magnetostrictive ultrasonic transducer using the magnetostrictive effect of a magnetic material, a piezoelectric ultrasonic transducer using the piezoelectric effect of a piezoelectric material, or a capacitive micromachined ultrasonic transducer (CMUT) that transmits and receives ultrasonic waves using vibration of several hundreds or thousands of micromachined thin films.

The ultrasonic transducers 118 may have a linear array or a convex array. A cover (not shown) for covering the ultrasonic transducers 118 may be provided above the ultrasonic transducers 118.

The light source 119 is used to irradiate light to the inside of the object. For example, the light source 119 may be at least one light source of generating a specific wavelength of light. As another example, the light source 119 may be a plurality of light sources of generating different wavelengths of light. The wavelength of light generated by the light source 119 may be selected in consideration of a target in the object. The light source 119 may be a Laser Diode (LD), a Light Emitting Diode (LED), a solid-state laser, a gas laser, optical fiber, or a combination thereof.

The probe 110 may be used to acquire at least ones of photoacoustic images and ultrasonic images.

For example, the probe 110 may be used to acquire only ultrasonic images. In this case, the plurality of ultrasonic transducers 118 installed in the probe 110 generate ultrasonic signals according to a control signal received from the main body 100, and irradiate the ultrasonic signals to the object. Then, the ultrasonic transducers 118 receive ultrasonic echo signals reflected from specific tissue (for example, lesions) in the object. At this time, the light source 119 is maintained in an off state.

As another example, the probe 110 may be used to acquire only photoacoustic images. In this case, the light source 119 of the probe 110 irradiates light to the object, and the ultrasonic transducers 118 receive photoacoustic signals generated from tissue that has absorbed the light.

As another example, the probe 110 may be used to acquire both ultrasonic images and photoacoustic images. In this case, the ultrasonic transducers 118 and the light source 119 included in the probe 110 may operate alternately at regular time intervals. For example, during a predetermined time period, the ultrasonic transducers 118 irradiate ultrasonic signals to an object, and receive ultrasonic echo signals reflected from specific tissue in the object. Then, during the following predetermined time period, the light source 119 irradiates light to the object, and the ultrasonic transducers 118 receive photoacoustic signals generated from tissue that has absorbed the light.

Whether to acquire only ultrasonic images, only photoacoustic images, or both ultrasonic images and photoacoustic images may be set by a user. A user may set a value instructing whether to acquire only ultrasonic images, only photoacoustic images, or both ultrasonic images and photoacoustic images, before starting diagnosis. For example, the value set by the user may be set not to change during diagnosis. As another example, the value set by the user may be implemented to allow a user to change the value during diagnosis. In the following description, it is assumed that both ultrasonic images and photoacoustic images are acquired using the probe 110.

One end of the probe 110 is connected to the cable 112. One end of the cable 112 is connected to the male connector 114. The male connector 114 is physically coupled with one of the female connectors 116 of the main body 100.

In the top part of the main body 100, the control panel 150, the sub display unit 170, and the main display unit 160 may be provided.

The sub display unit 170 displays applications related to operations of the medical imaging apparatus. For example, the sub display unit 170 may display menus or guidance for ultrasonography. The sub display unit 170 may be implemented as a Cathode Ray Tube (CRT), a Liquid Crystal Display (LCD), or a LED display. The sub display unit 170 may be omitted. In this case, applications, menus, etc., which are displayed through the sub display unit 170, may be displayed through the main display unit 160 which will be described below.

The main display unit 160 may display images acquired during diagnosis, and a User Interface (UI) for helping a user manipulate the medical imaging apparatus.

The images acquired during diagnosis may be ultrasonic images, photoacoustic images, and thumbnail images. The ultrasonic images may be B-mode images, C-mode images, M-mode images, D-mode images, or elasticity images.

The thumbnail images may be thumbnail images corresponding to the ultrasonic images, thumbnail images corresponding to the photoacoustic images, or thumbnail images corresponding to both the ultrasonic images and the photoacoustic images. A method of displaying the images and the UI will be described with reference to FIGS. 3A to 4D, later.

In FIG. 1, the main display unit 160 is positioned above the sub display unit 170. The main display unit 160 may be, like the sub display unit 170, implemented as one of a CRT, a LCD, a LED display, and a touch screen. In FIG. 1, a case in which the main display unit 160 is coupled with the control panel 150 at the upper part is shown. However, the main display unit 160 may be mechanically separated from the control panel 150.

As illustrated in FIG. 1, the main display unit 160 and the sub display unit 170 are arranged on the control panel 150. Accordingly, when the control panel 150 moves, the main display unit 160 and the sub display unit 170 move together with the control panel 150.

The control panel 150 is disposed in the top part of the main body 100. The control panel 150 may be implemented to allow a left-and-right horizontal movement, a back-and-forth horizontal movement, and an up-and-down vertical movement.

The control panel 150 receives commands related to operations of the medical imaging apparatus. For example, the control panel 150 may receive a command instructing whether to acquire only ultrasonic images, only photoacoustic images, or both ultrasonic images and photoacoustic images through the probe 110. Also, the control panel 150 may receive a command selecting a single mode of displaying only photoacoustic images among ultrasonic images and photoacoustic images in a first region, or a command selecting a dual mode of displaying both ultrasonic images and photoacoustic images in a first region.

In order to receive a command from a user, the control panel 150 may include at least one(s) among a key(s), a button(s), a wheel, a joystick, a trackball, and a knop. A command input through the control panel 150 may be transmitted to the main body 100 through wired/wireless communication.

In one side of the control panel 150, one or more probe holders 152 may be provided. The user may put the probe 110 into one of the probe holders 152 to safely keep the probe 110 when he/she does not use the medical imaging apparatus. In FIG. 1, the probe holders 152 have different sizes, however, the probe holders 152 may have different sizes and/or shapes. For example, the probe holders 152 may have various sizes and/or shapes according to the size and/or shape of the probe 110.

In one side of the control panel 150, a handle part 180 for adjusting the location of the control panel 150 is provided. The user holds the handle part 180 with his/her hand to apply a force in a front-rear, left-right, or up-down direction, thus moving the control panel 150 to the front or rear, to the left or right, or up or down. For example, the location of the control panel 150 may be manually adjusted. As another example, the location of the control panel 150 may be automatically adjusted according to an external force applied to the control panel 150 by sensing the external force.

The external appearance of the medical imaging apparatus has been described. Hereinafter, a control configuration of the medical imaging apparatus, according to an embodiment of the present invention, will be described with reference to FIG. 2.

FIG. 2 is a block diagram of a control configuration of the medical imaging apparatus illustrated in FIG. 1.

Referring to FIG. 2, the medical imaging apparatus includes a transmission signal generator 104, a probe 110, a beamformer 101, a sensing unit 103, a control panel 150, a storage unit 105, a main display unit 160, a sub display unit 170, and a controller 190. Detailed descriptions about components described above with reference to FIG. 1 among the above-mentioned components will be omitted.

The transmission signal generator 104 may generate a transmission signal in consideration of the locations and focusing points of the ultrasonic transducers 118 (see FIG. 1). Herein, the transmission signal is a high-voltage electrical signal for vibrating the ultrasonic transducers 118. The transmission signal may be transmitted to the ultrasonic transducers 118 of the probe 110.

The ultrasonic transducers 118 of the probe 110 may convert the transmission signal into an ultrasonic signal, irradiate the ultrasonic signal to an object, and receive ultrasonic echo signals from the object. The received ultrasonic echo signals may be transmitted to the beamformer 101.

Also, the ultrasonic transducers 118 may receive photoacoustic signals due to a photoacoustic effect. That is, if light generated by the light source 119 is irradiated to an object, tissue that has absorbed the light generates photoacoustic signals, and the ultrasonic transducers 118 may receive the photoacoustic signals. The received photoacoustic signal may be transmitted to the beamformer 101.

The beamformer 101 may convert the ultrasonic echo signals which are analog signals into digital signals. Also, the beamformer 101 delays the digital signals in consideration of the locations and focusing points of the ultrasonic transducers 118, and focuses the resultant digital signals to generate a received, focused signal. The received, focused signal generated by the beamformer 101 can be understood as a section image of the object.

The sensing unit 103 senses the location of the probe 110. For example, the sensing unit 103 may be an absolute position sensor. In this case, the sensing unit 103 senses the location of the probe 110 with respect to a fixed point. As another example, the sensing unit 103 may be a relative position sensor. In this case, the sensing unit 103 may sense the location of the probe 110 with respect to an arbitrary point. The sensing unit 103 may be provided inside or outside the probe 110. Information about the location of the probe 110, sensed by the sensing unit 103, may be stored in the storage unit 105 together with ultrasonic images, photoacoustic images, and thumbnail images produced by the controller 190.

The controller 190 produces an ultrasonic image based on ultrasonic echo signals reflected from a target in the object. Also, the controller 190 produces a photoacoustic image based on the photoacoustic effect generated from the target in the object.

According to an embodiment, the user may scan an object twice using the probe 110. In the following description, an ultrasonic image and a photoacoustic image acquired by initially scanning an object are referred to as a "first ultrasonic image" and a "first photoacoustic image", respectively, and an ultrasonic image and a photoacoustic image acquired by secondarily scanning the object are referred to as a "second ultrasonic image" and a "second photoacoustic image", respectively.

The controller 190 produces one or more thumbnail images for at least one of the first ultrasonic image and the first photoacoustic image. The produced thumbnail images are arranged according to predetermined criteria, and displayed in a display area of the main display unit 160.

Also, the controller 190 may generate an UI (for example, an icon) for helping the user manipulate the medical imaging apparatus. Herein, the icon is text or a figure representing predetermined information. In addition to generating an icon, the controller 190 may highlight a selected icon and/or a selected image.

The controller 190 may highlight thumbnail images that are identical to a second ultrasonic image and a second photoacoustic image, among produced thumbnail images.

The storage unit 105 may store data or algorithms needed for operations of the medical imaging apparatus, a first ultrasonic image and a first photoacoustic image produced by the controller 190, the photoacoustic signal intensity of a target selected from the first photoacoustic image, thumbnail images, information about the location of the probe 110 when the first ultrasonic image and the first photoacoustic image have been acquired, etc. The above-mentioned data may be stored in the form of a look-up table.

The storage unit 105 may be a non-volatile memory device such as Read Only Memory (ROM), Random Access Memory (RAM), Programmable Read Only Memory (PROM), Erasable Programmable Read Only Memory (EPROM), or flash memory, a volatile memory device such as Random Access Memory (RAM), storage media such as a hard disk, or an optical disk. However, the storage unit 105 is not limited to these, and may be any other storage device well-known in the art.

Hereinafter, a method of displaying images and UIs produced by the medical imaging apparatus will be described.

First, a method of displaying images and UIs produced during initial scanning will be described with reference to FIGS. 3A to 3D, below.

FIGS. 3A to 3D illustrate screens displayed in display areas 31 and 32 when an object has been initially scanned.

If an object is initially scanned, the controller 190 (see FIG. 2) produces a first ultrasonic image 310a and a first photoacoustic image 310b. The first ultrasonic image 310a and the first photoacoustic image 310b are displayed in a dual mode in the first area 31 of the display areas 31 and 32, which is illustrated in FIG. 3A.

Since the first ultrasonic image 310a and the first photoacoustic image 310b have been simultaneously acquired, they may show the same pattern of targets. However, targets included in the first ultrasonic image 310a are represented with gray scales according to the intensities of ultrasonic echo signals reflected from the corresponding real targets, whereas targets included in the first photoacoustic image 310b are represented with different colors according to the intensities of photoacoustic signals generated from the corresponding real targets.

Figure 3A:
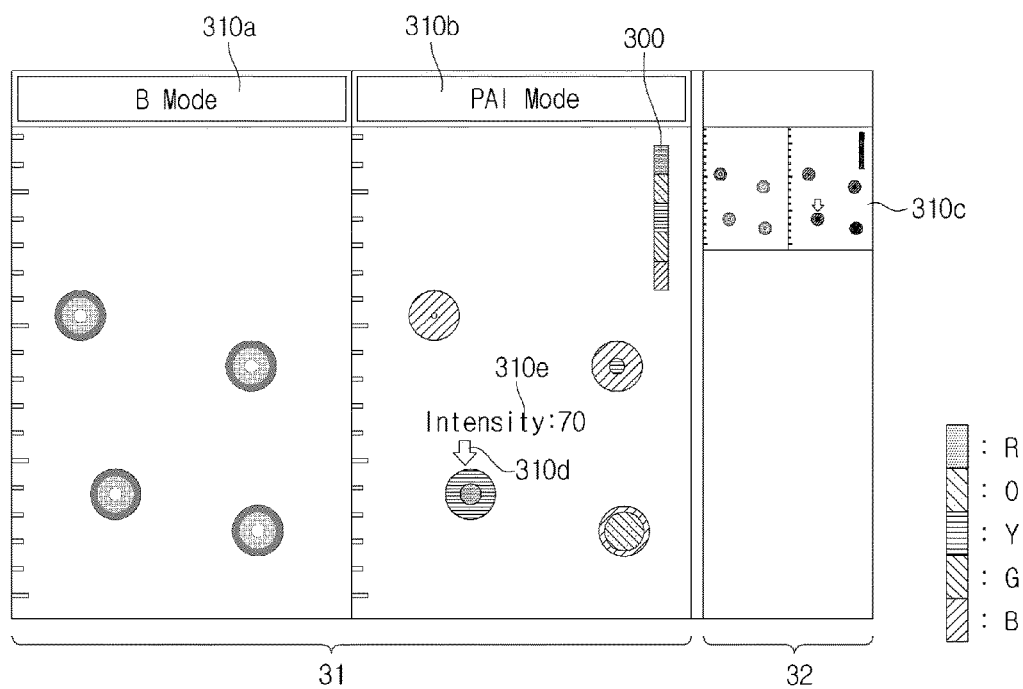
FIGS. 3A to 3D illustrate screens displayed on display areas when an object has been initially scanned.

In FIG. 3A, a color bar 300 is displayed to partially overlap the first photoacoustic image 310b. Different colors of the color bar 300 represent different intensities of photoacoustic signals.

The color bar 300 includes a blue color B, a green color G, a yellow color Y, an orange color O, and a red color R in order from bottom to top. If the intensity of a photoacoustic signal generated by a target in the object is great, the corresponding target is displayed with the red color R in the first photoacoustic image 310b. If the intensity of a photoacoustic signal generated by a target in the object is small, the corresponding target is displayed with the blue color B in the first photoacoustic image 310b.

As such, since the color bar 300 is displayed to partially overlap the first photoacoustic image 310b, a user can easily recognize photoacoustic signal intensities of the targets included in the first photoacousic image 310.

Meanwhile, the greater photoacoustic signal intensity of a target, the higher probability that the target is tissue (that is, a lymph node) that is desired to be detected. Accordingly, it is necessary to set a target having the greatest photoacoustic signal intensity, among the targets included in the first photoacoustic image 310b, to a region of interest. Operation of selecting a target in the first photoacoustic image 310b may be manually performed. In this case, the user uses an input device, such as the control panel 150 (see FIG. 1) or a mouse (not shown), or touches the first area 31 with his/her finger to select a desired target. As another example, operation of selecting a target in the first photoacoustic image 310b may be automatically performed. In this case, the photoacoustic signal intensities of the targets included in the first photoacoustic image 310b are analyzed to automatically select a target having the greatest photoacoustic signal intensity.

If a target is selected from the first photoacoustic image 310b, the controller 190 generates an icon related to the selected target. More specifically, the controller 190 generates at least one of an icon 310d indicating the selected target and an icon 310e representing the photoacoustic signal intensity of the selected target. The generated icons 310d and 310e are displayed around the selected target. In FIG. 3A, both the icon 310d indicating the selected target and the icon 310e representing the photoacoustic signal intensity of the selected target are displayed around the selected target. The photoacoustic signal intensity of the target selected from the first photoacoustic image 310b may be used to arrange thumbnail images.

After a target is selected from the first photoacoustic image 310b, the controller 190 produces thumbnail images 310c corresponding to the first ultrasonic image 310a and the first photoacoustic image 310b.

If the thumbnail images 310c are produced, the controller 190 may arrange the thumbnail images 310c and previously produced thumbnail images according to predetermined criteria. More specifically, the controller 190 arranges thumbnail images produced up to now, according to the photoacoustic signal intensities of a selected target in first photoacoustic images acquired up to now. The arranged thumbnail images are displayed in the second area 32 of the main display 160 (see FIG. 2). Operation of arranging and displaying thumbnail images will be described in more detail, below.

In FIG. 3A, the first ultrasonic image 310a and the first photoacoustic image 310b initially acquired during the initial scanning, and their thumbnail images 310c are shown. The first ultrasonic image 310a and the first photoacoustic image 310b are displayed side by side in the first area 31. Referring to the icons 310d and 310e displayed around the selected target in the first photoacoustic image 310b, the photoacoustic signal intensity of the selected target is 70. The thumbnail images 310c of the first ultrasonic image 310a and the first photoacoustic image 310b are displayed in the top of the second area 32.

Figure 3B:
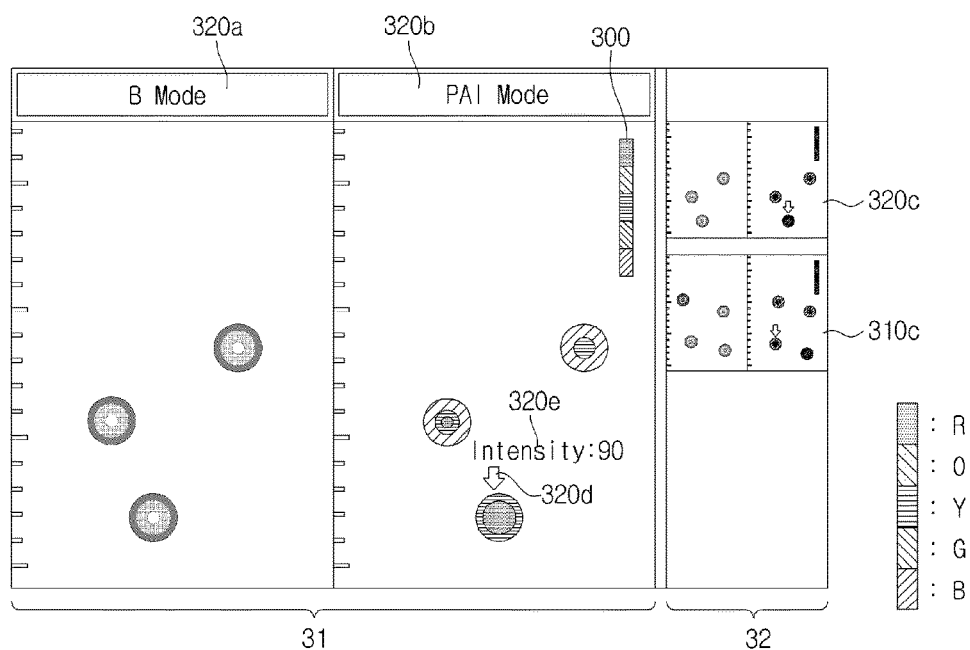

In FIG. 3B, a first ultrasonic image 320a and a first photoacoustic image 320b secondarily acquired during the initial scanning, and their thumbnail images 320c are shown. The first ultrasonic image 320a and the first photoacoustic image 320b are displayed side by side in the first area 31. Also, in the second area 32, the thumbnail images 320c of the first ultrasonic image 320a and the first photoacoustic image 320b, and the previously produced thumbnail images 310c are arranged. The second thumbnail images 320c of the first ultrasonic image 320a and the first photoacoustic image 320b are disposed above the previously produced thumbnail images 310c. The reason is because the photoacoustic signal intensity "90" of the selected target in the first photoacoustic image 320b secondarily acquired is greater than the photoacoustic signal intensity "70" of the selected target in the first photoacoustic image 310b initially acquired.

Figure 3C:
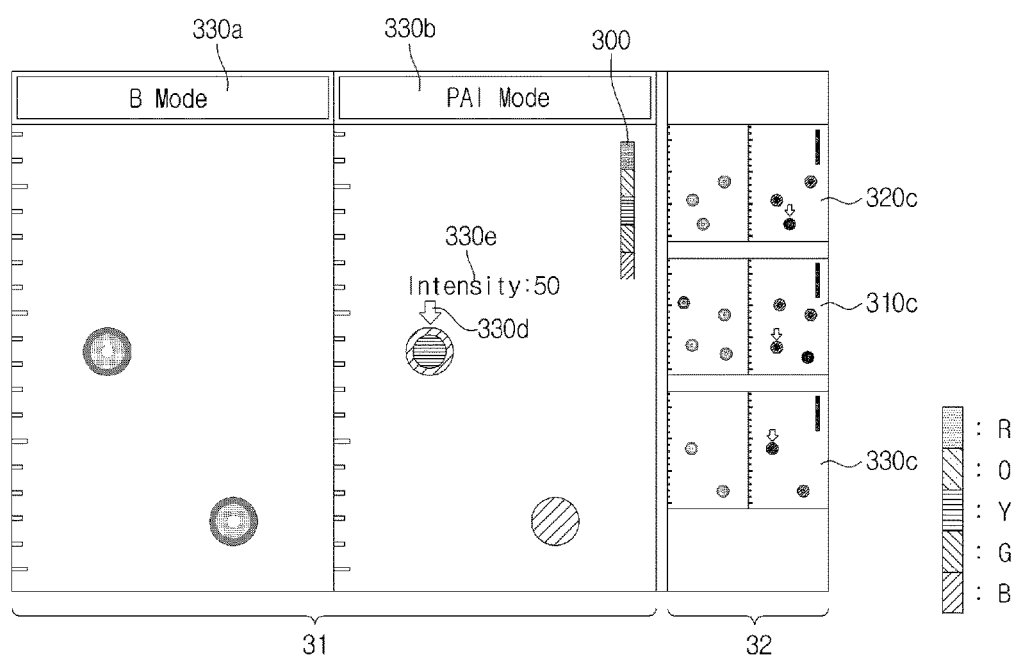

In FIG. 3C, a first ultrasonic image 330a and a first photoacoustic image 330b thirdly acquired during the initial scanning, and their thumbnail images 330c are shown. The first ultrasonic image 330a and the first photoacoustic image 330b are displayed side by side in the first area 31. Also, in the second area 32, the thumbnail images 330c of the first ultrasonic image 330a and the first photoacoustic image 330b, and the previously produced thumbnail images 310c and 320c are arranged. The thumbnail images 330c of the first ultrasonic image 330a and the first photoacoustic image 330b are arranged below the previously produced thumbnail images 310c. The reason is because the photoacoustic signal intensity "50" of the selected target in the first photoacoustic image 330b thirdly acquired is smaller than the photoacoustic signal intensity "70" of the selected target in the first photoacoustic image 310b first acquired.

Figure 3D:
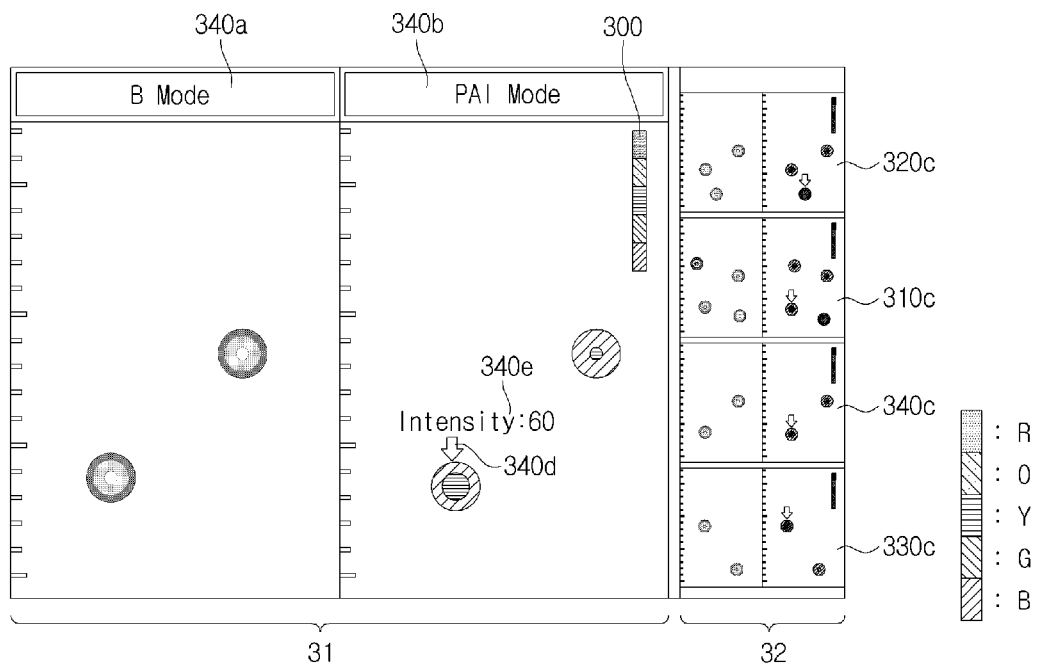

In FIG. 3D, a first ultrasonic image 340a and a first photoacoustic image 340b fourthly acquired during the initial scanning, and their thumbnail images 340c are shown. The first ultrasonic image 340a and the first photoacoustic image 340b are displayed side by side in the first area 31. Also, in the second area 32, the thumbnail images 340c of the first ultrasonic image 340a and the first photoacoustic image 340b, and the previously produced thumbnail images 310c, 320c, and 330c are arranged. The thumbnail images 340c of the first ultrasonic image 340a and the first photoacoustic image 340b are arranged between the thumbnail images 310c and the thumbnail images 330c. The reason is because the photoacoustic signal intensity "60" of the selected target in the first photoacoustic image 340b fourthly acquired is smaller than the photoacoustic signal intensity "70" of the selected target in the first photoacoustic image 310b initially acquired, and greater than the photoacoustic signal intensity "50" of the selected target in the first photoacoustic image 330b thirdly acquired.

Hereinafter, a method of displaying images and UIs acquired during secondary scanning will be described with reference to FIGS. 4A to 4D.

FIGS. 4A to 4D illustrate screens displayed through the main display unit 160 (see FIG. 2) when an object has been secondarily scanned.

Figure 4A:
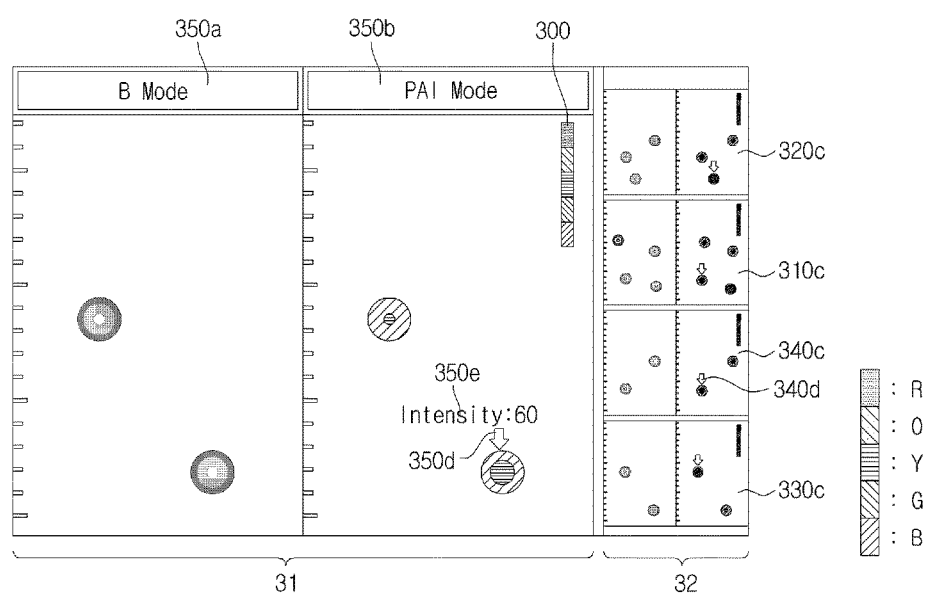
FIGS. 4A to 4D illustrate screens displayed in display areas when an object has been secondarily scanned.

If an object is secondarily scanned through the probe 110 (see FIG. 1), the controller 190 (see FIG. 2) produces a second ultrasonic image 350a and a second photoacoustic image 350b. The second ultrasonic image 350a and the second photoacoustic image 350b are displayed in a dual mode in the first area 31 of the main display unit 160, as illustrated in FIG. 4A.

Thereafter, a target is selected from the second photoacoustic image 350b. Operation of selecting a target from the second photoacoustic image 350b may be manually or automatically performed. When a target is manually selected, a user uses an input device, such as the control panel 150 (see FIG. 1) or a mouse (not shown), or touches the first area 31 with his/her finger to select a desired target. When a target is automatically selected, the photoacoustic signal intensities of targets included in the second photoacoustic image 350*b* are analyzed to automatically select a target having the greatest photoacoustic signal intensity.

If a target is selected from the second photoacoustic image 350*b*, the controller 190 generates at least one of an icon 350*d* indicating the selected target and an icon 350*e* representing the photoacoustic signal intensity of the selected target. The generated icons 350*d* and 350*e* are displayed around the selected target, as illustrated in FIG. 4A.

Thereafter, the controller 190 selects thumbnail images (that is, the thumbnail images 340*c*) including a target having the same photoacoustic signal intensity as that of the selected target in the second photoacoustic image 350*b*, from among the thumbnail images 310*c*, 320*c*, 330*c*, and 340*c* displayed in the second area 32.

Figure 4B:
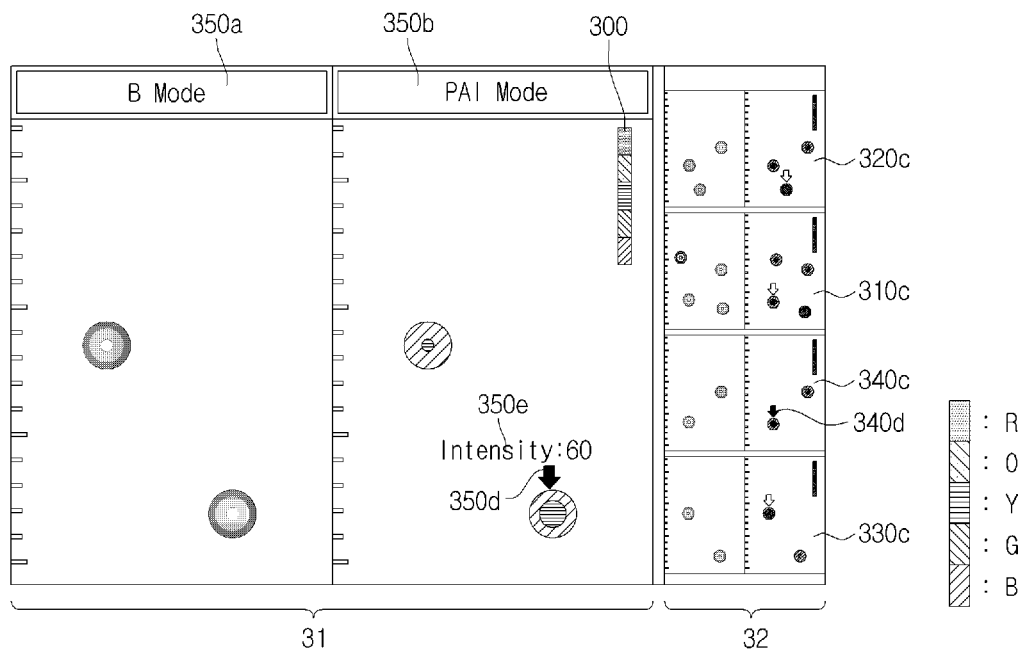

If the thumbnail images 340*c* are selected, the controller 190 highlights the icon 340*d* indicating the target of the selected thumbnail images 340*c*, and the icon 350*d* indicating the selected target in the second photoacoustic image 350*b*, which is illustrated in FIG. 4B. In FIG. 4B, the color of the icon 340*d* indicating the target of the selected thumbnail images 340*c* is displayed with a different color from that of the icons 310*d*, 320*d*, and 330*d* indicating the targets of the remaining thumbnail images 310*c*, 320*c*, and 330*c*, thereby enhancing the icon 340*d*. Also, in FIG. 4B, the icon 340*d* of the thumbnail images 340*c* and the icon 350*d* of the second photoacoustic image 350*b* are highlighted with the same color.

Thereafter, the controller 190 compares information about the location of the probe 110 (see FIG. 1) when the selected thumbnail images 340*c* have been acquired, to information (that is, information about the current location of the probe 110) about the location of the probe 110 when the second photoacoustic image 350*b* has been acquired. Then, the controller 190 generates icons 360 representing information for location adjustment of the probe 110 based on the result of the comparison. The icons 360 are displayed to partially overlap the second photoacoustic image 350*b*, which illustrated in FIG. 4C. The icons 360 representing information for location adjustment of the probe 110 will be described with reference to FIG. 5, later.

As described above, if the icons 360 representing information for location adjustment of the probe 110 are displayed, the user can adjust the location of the probe 110 based on the displayed icons 360.

If the user adjusts the location of the probe 110 so as to make the current location of the probe 110 identical to the location of the probe 110 when the thumbnail images 340*c* have been acquired, the number and shapes of the icons 360 may change. As such, by making the current location of the probe 110 identical to the location of the probe 110 when the thumbnail images 340*c* have been acquired, a probability that the same second ultrasonic image and second photoacoustic image as the thumbnail images 340*c* will be acquired increases.

Figure 4C:
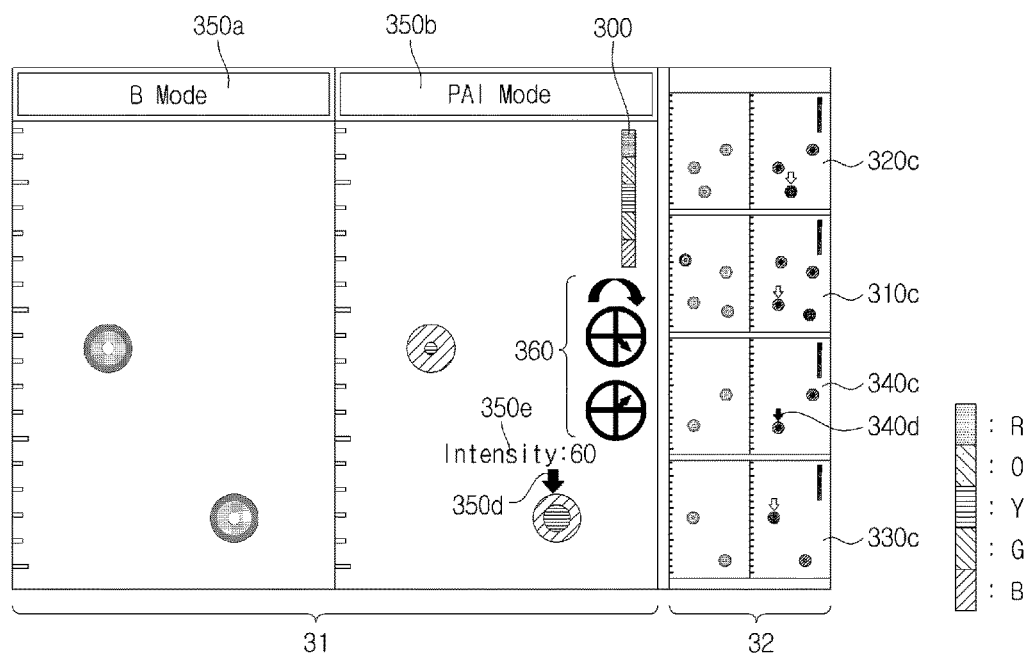
Figure 4D:
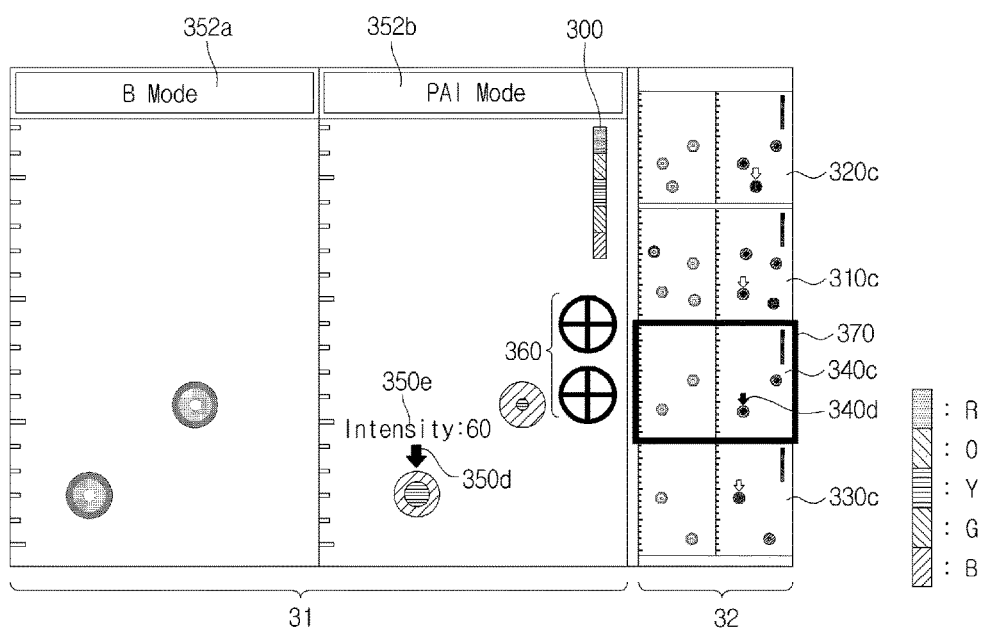

After the location adjustment of the probe 110 is completed, the controller 190 displays a second ultrasonic image 352*a* and a second photoacoustic image 352*b* acquired after the location adjustment of the probe 110, in the first area 31, which is illustrated in FIG. 4D. Hereinafter, the second ultrasonic image 352*a* and the second photoacoustic image 352*b* acquired after the location adjustment of the probe 110 are referred to as a "third ultrasonic image" and a "third photoacoustic image".

Thereafter, the controller 190 determines whether the third ultrasonic image 352*a* and the third photoacoustic image 352*b* are identical to the first ultrasonic image 340*a* and the first photoacoustic image 340*b* of the selected thumbnail images 340*c*. The determination may be done in various methods.

For example, the controller 190 may compare the photoacoustic signal intensities of targets included in the third photoacoustic image 352*b*, to the photoacoustic signal intensities of targets included in the first photoacoustic image 340*b* of the thumbnail images 340*c*. In addition, the controller 190 may compare ultrasonic echo signal intensities of targets included in the third ultrasonic image 352*a*, to ultrasonic echo signal intensities of targets included in the first ultrasonic image 340*a* of the thumbnail images 340*c*. As such, by comparing ultrasonic images to each other, as well as photoacoustic images, the reliability of the results of the comparison can be improved compared to when only photoacoustic images are compared to each other.

As another example, the controller 190 may compare a pattern of the targets included in the third photoacoustic image 352*b*, to a pattern of the targets included in the first photoacoustic image 340*b* of the thumbnail images 340*c*.

If it is determined based on the results of the comparison that the third ultrasonic image 352*a* and the third photoacoustic image 352*b* are identical to the first ultrasonic image 340*a* and the first photoacoustic image 340*b* of the thumbnail images 340*c*, the controller 190 may highlight the selected thumbnail images 340*c*, which is illustrated in FIG. 4D.

The selected thumbnail images 340*c* may be highlighted in various methods. For example, the controller 190 may draw lines having a predetermined shape, a predetermined thickness, and a predetermined color around the edges of the selected thumbnail images 340*c*. As another example, the controller 190 may display an icon (not shown) such as an arrow around the selected thumbnail images 340*c*. As another example, the controller 190 may enlarge the selected thumbnail images 340*c* at a predetermined ratio, and reduce the remaining thumbnail images 310*c*, 320*c*, and 330*c* at a predetermined ratio. However, a method of highlighting the selected thumbnail images 340*c* is not limited to these.

Figure 5:
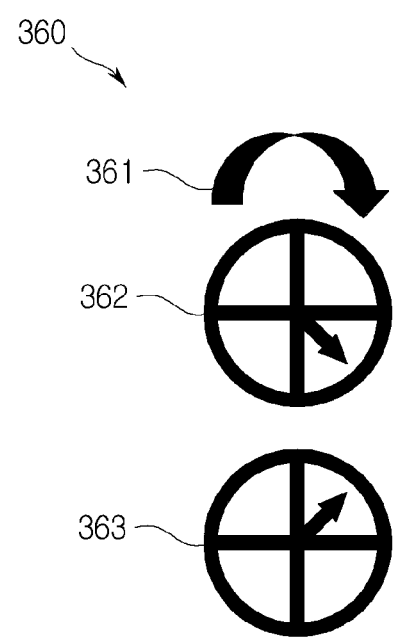
FIG. 5 illustrates icons representing information for location adjustment of a probe.

FIG. 5 is an enlarged view of the icons 360 representing information for location adjustment of the probe 110 (see FIG. 1). The icons 360 may include at least one of an icon 361 representing a direction of rotation, an icon 362 representing distance information, and an icon 363 representing angle information.

The icon 361 representing the direction of rotation informs of a direction in which the probe 110 needs to rotate. The icon 361 may be represented as an arrow. In FIG. 5, the icon 361 represents that the probe 110 needs to rotate clockwise from its current position. If the probe 110 does not need to rotate, the icon 361 may be omitted.

The icon 362 representing the distance information informs of a direction and a distance in which and by which the probe 110 needs to move. The icon 362 may be represented as a circle with a cross inside. In this case, the center of the circle may correspond to the current location of the probe 110. Information about the direction and the distance in which and by which the probe 110 needs to move may be represented as an arrow. In detail, the direction of the arrow may represent a direction in which the probe 110 needs to move, and the length of the arrow may represent a distance by which the probe 110 needs to move. In FIG. 5, the icon 362 represents that the probe 110 needs to move by a predetermined distance in the down and right direction. If the probe 110 does not need to move, the icon 362 will include no arrow.

The icon 363 representing the angle information informs of a direction and an angle in which and at which the probe 110 needs to tilt. The icon 363 may be represented as a circle with a cross inside. In this case, the center of the circle may correspond to the current position of the probe 110. The direction and the angle in which and at which the probe 110 needs to tilt may be represented as an arrow. In detail, the direction of the arrow may represent a direction in which the probe 110 needs to tilt, and the length of the arrow may represent an angle at which the probe 110 needs to tilt. In FIG. 5, the icon 363 represents that the probe 110 needs to tilt at a specific angle in the up and right direction. If the probe 110 does not need to tilt, the icon 363 will include no arrow.

FIG. 6 is a flowchart of a medical image providing method according to an embodiment of the present invention.

Referring to FIGS. 3A to 3D, 4A to 4D, and 5, an object is initially scanned to acquire a first ultrasonic image 340a and a first photoacoustic image 340b, and the first ultrasonic image 340a and the first photoacoustic image 340b are displayed in the first area 31 of the display areas 31 and 32 (S611).

Then, a target that is to be set to a region of interest is selected from the first photoacoustic image 340b (S612). The target may be selected manually by a user, or automatically according to a photoacoustic signal intensity.

If a target is selected from the first photoacoustic image 340b, icons related to the selected target are displayed. For example, as illustrated in FIG. 3D, an icon 340d indicating the selected target, and an icon 340e representing the photoacoustic signal intensity of the selected target are displayed around the selected target (S613).

Thereafter, thumbnail images 340c of the first ultrasonic image 340a and the first photoacoustic image 340b are displayed in the second area 32 of the main display unit 160 (see FIG. 2) (S614). Operation S614 includes operations of: producing the thumbnail images 340c of the first ultrasonic image 340a and the first photoacoustic image 340b; arranging the produced thumbnail images 340c and the previously produced thumbnail images 310c, 320c and 330c according to the photoacoustic signal intensities of targets respectively selected from the first photoacoustic images 310b, 320b, 330b and 340b acquired up to now; and displaying the arranged thumbnail images 310c, 320c, 330c and 340c in the second area 32 of the display areas 31 and 32.

Thereafter, the object is secondarily scanned to acquire a second ultrasonic image 350a and a second photoacoustic image 350b, and the second ultrasonic image 350a and a second photoacoustic image 350b are displayed in the first area 31 of the display areas 31 and 32, as illustrated in FIG. 4A (S621).

Then, a target that is to be set to a region of interest is selected from the second photoacoustic image 350b (S622).

If a target is selected from the second photoacousic image 350b, icons related to the selected target are displayed (S623). For example, as illustrated in FIG. 4A, an icon 350d indicating the selected target and an icon 350e representing the photoacoustic signal intensity of the selected target are displayed around the selected target (S623).

Then, thumbnail images (for example, the thumbnail images 340c) including a target having the same photoacoustic signal intensity as that of the selected target in the second photoacoustic image 350b are selected from among thumbnail images 310c, 320c, 330c, and 340c displayed in the second area 32 (S624). If the thumbnail images 340c are selected, as illustrated in FIG. 4B, an icon 340d indicating the target of the selected thumbnail images 340c and an icon 350d indicating the selected target in the second photoacoustic image 350b may be highlighted.

Then, as illustrated in FIG. 4C, icons 360 representing information for location adjustment of the probe 110 (see FIG. 2) are displayed (S625). Operation S625 includes operations of: receiving information about the current location of the probe 110 from the sensing unit 103 (see FIG. 2); comparing the received information about the current location of the probe 110 to information about the location of the probe 110 when the thumbnail images 340c have been acquired; generating icons 360 representing information for location adjustment of the probe 110 according to the results of the comparison; and displaying the icons 360 in such a way to partially overlap the second photoacoustic image 350b.

Then, a user can adjust the location of the probe 110 based on the icons 360 (S626). If the location of the probe 110 is adjusted, the number and shapes of the icons 360 may change. In FIG. 4D, a case in which information about the location of the probe 110, received from the sensing unit 103, is identical to information about the location of the probe 110 when the thumbnail images 340c have been acquired is shown. The icons 360 illustrated in FIG. 4D are different from the icons 360 illustrated in FIG. 4C, in that the icons 360 illustrated in FIG. 4D include no icon 361 representing a direction of rotation, and both the icon 362 representing distance information and the icon 363 representing angle information include no arrow.

If the location adjustment of the probe 110 is completed, a third ultrasonic image 352a and a third photoacoustic image 352b acquired after the location adjustment of the probe 110 are displayed in the first area 31.

Then, the third ultrasonic image 352a and the third photoacoustic image 352b are compared to the selected thumbnail images 340c (S627). That is, it is determined whether the third ultrasonic image 352a and the third photoacoustic image 352b are identical to the first ultrasonic image 340a and the first photoacoustic image 340a of the selected thumbnail images 340c. Operation S627 may include at least one of operations of: comparing the third ultrasonic image 352a to the first ultrasonic image 340a of the thumbnail images 340c; and comparing the third photoacoustic image 352b to the first photoacoustic image 340b of the thumbnail images 340c.

If it is determined that the third ultrasonic image 352a and the third photoacoustic image 352b are identical to the first ultrasonic image 340a and the first photoacoustic image 340b of the selected thumbnail images 340c, the selected thumbnail images 340c are highlighted, as illustrated in FIG. 4D (S628).

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A medical imaging apparatus comprising:
a probe configured to acquire photoacoustic images by scanning an object using the probe;
a sensor configured to sense a location of the probe;
a display configured to arrange, display, and highlight thumbnail images; and
a controller configured to:
control the probe to acquire n first photoacoustic images via an initial scan of the object using the probe,
receive, from the sensor, sensed locations of the probe for acquisitions of the n first photoacoustic images respectively,
generate n thumbnail images corresponding to the n first photoacoustic images,
control the display to arrange and display the n thumbnail images,
control the probe to acquire a second photoacoustic image via a secondary scan of the object using the probe,
receive, from the sensor, a sensed location of the probe for the acquisition of the second photoacoustic image,
identify a thumbnail image, from among the n thumbnail images, that is identical to the second photoacoustic image based on the sensed locations of the probe for acquisitions of the n first photoacoustic images and the sensed location of the probe for the acquisition of the second photoacoustic image, and
control the display to visually highlight the identified thumbnail image.

2. The medical imaging apparatus according to claim 1, wherein the controller is configured to:
receive a selection of targets in the n first photoacoustic images, and
control the display to display at least one of an icon representing a photoacoustic signal intensity of each of the selected targets and an icon around each of the selected targets indicating the selection of each of the selected targets.

3. The medical imaging apparatus according to claim 1, wherein the controller is configured to:
receive a selection of targets in the n first photoacoustic images, and
control the display to display the n thumbnail images arranged in an order according to photoacoustic signal intensities of the n first photoacoustic images at the respective targets.

4. The medical imaging apparatus according to claim 1, wherein the controller is configured to:
select a thumbnail image including a target having the same photoacoustic signal intensity as that of a target selected from the second photoacoustic image, from among the n thumbnail images;
compare information about a location of the probe when the selected thumbnail image has been acquired, to information about a location of the probe when the second photoacoustic image has been acquired, and control the display to display an icon representing information for location adjustment of the probe based on the result of the comparison;
if a location of the probe is adjusted based on the icon, compare a third photoacoustic image acquired after the location adjustment of the probe to the selected thumbnail image; and
if the third photoacoustic image is identical to the selected thumbnail image, control the display to visually highlight the selected thumbnail image.

5. The medical imaging apparatus according to claim 4, wherein the controller is configured to control the display to display at least one icon of an icon indicating the selected target in the second photoacoustic image and an icon representing a photoacoustic signal intensity of the selected target.

6. The medical imaging apparatus according to claim 4, wherein the controller is configured to control the display to visually highlight at least one icon of an icon indicating the target of the thumbnail image and an icon indicating the selected target in the second photoacoustic image.

7. The medical imaging apparatus according to claim 4, wherein the icon representing information for location adjustment of the probe includes at least one icon of:
an icon representing information about a direction in which the probe needs to rotate; an icon representing information about a direction and a distance in which and by which the probe needs to move; and an icon representing information about a direction and an angle in which and at which the probe needs to tilt.

8. The medical imaging apparatus according to claim 4, wherein the controller is configured to compare the third photoacoustic image and an ultrasonic image acquired simultaneously with the third photoacoustic image to the selected thumbnail image.

9. The medical imaging apparatus according to claim 4, wherein the controller is configured to compare a photoacoustic signal intensity of a target included in the third photoacoustic image to a photoacoustic signal intensity of the corresponding target included in the selected thumbnail image.

10. The medical imaging apparatus according to claim 4, wherein the controller is configured to compare a pattern of targets included in the third photoacoustic image to a pattern of targets included in the selected thumbnail image.

* * * * *